(12) United States Patent
Mailland

(10) Patent No.: US 8,680,074 B2
(45) Date of Patent: Mar. 25, 2014

(54) USE OF CHITOSANS TO INCREASE NAIL GROWTH RATE

(75) Inventor: Federico Mailland, Milan (IT)

(73) Assignee: Polichem SA, Luxembourg (LU)

( * ) Notice: Subject to any disclaimer, the term of this patent is extended or adjusted under 35 U.S.C. 154(b) by 23 days.

(21) Appl. No.: 12/449,573

(22) PCT Filed: Feb. 7, 2008

(86) PCT No.: PCT/EP2008/051477
§ 371 (c)(1),
(2), (4) Date: Feb. 16, 2010

(87) PCT Pub. No.: WO2008/098869
PCT Pub. Date: Aug. 21, 2008

(65) Prior Publication Data
US 2010/0152133 A1    Jun. 17, 2010

(30) Foreign Application Priority Data
Feb. 14, 2007    (EP) .................................... 07102335

(51) Int. Cl.
| | | |
|---|---|---|
| *A61K 8/73* | (2006.01) | |
| *A61K 31/722* | (2006.01) | |
| *A61Q 3/00* | (2006.01) | |
| *A61Q 3/02* | (2006.01) | |
| A61K 31/4418 | (2006.01) | |
| A61K 31/58 | (2006.01) | |
| A61K 31/593 | (2006.01) | |
| A61K 45/06 | (2006.01) | |
| A61P 17/00 | (2006.01) | |
| A61P 31/10 | (2006.01) | |

(52) U.S. Cl.
USPC ............. 514/55; 424/61; 424/70.13; 424/401

(58) Field of Classification Search
None
See application file for complete search history.

(56) References Cited

U.S. PATENT DOCUMENTS

| | | | |
|---|---|---|---|
| 4,780,310 A | 10/1988 | Lang et al. | |
| 4,954,619 A * | 9/1990 | Lang et al. | ...................... 536/20 |
| 5,120,530 A | 6/1992 | Ferro | |
| 5,667,768 A | 9/1997 | Ramin | |
| 6,391,334 B1 * | 5/2002 | Zimmerman et al. | ........ 424/443 |

FOREIGN PATENT DOCUMENTS

| | | |
|---|---|---|
| EP | 1303249 | 3/2004 |
| EP | 1491202 | 12/2004 |
| RU | 2108114 | 4/1998 |
| WO | WO 02/07683 * | 1/2002 |
| WO | 03/051376 | 6/2003 |
| WO | 2004/064800 | 8/2004 |
| WO | WO2004112814 | 12/2004 |
| WO | 2006/011426 | 10/2006 |
| WO | 2007/042682 | 4/2007 |
| WO | 2008/049401 | 5/2008 |

OTHER PUBLICATIONS

Kumar, M. "A review of chitin and chitosan applications" Reactive & Functional Polym. (2000) vol 46, pp. 1-27.*
Geyer, A. et al "Modulation of linear nail growth . . ." J. Am. Acad. Dermatol. (2004) vol. 50, pp. 229-234.*
PubMed entry for "dexpanthenol" (2005) http://pubchem.ncbi.nlm.nih.gov/summary/summary.cgi?cid=4678&loc=ec_rcs#x299, retrieved from the Internet Oct. 13, 2013.*
J. Wenk, "Myfungar Nagellak (antifungal nail varnish) new water-soluble nail vanishtechnology" Haut, Vianital Verlag, Essen, vol. 15, No. 7, pp. 307-308, 2004.
Monti, et al., "In vitro tansungual permeation of ciclopirox from a hudroxypropyl chitosan-based, water-soluble nail lacquer" Drug Development and Industrial Pharmacy, Vo. 31, No. 1, pp. 11-17, 2005.
International Search Report for PCT/EP2008/051477 of Aug. 12, 2008.
I.P.E.R. for PCT/EP2008/051477 of May 22, 2009.
Muzzarelli, et al., "Chitosan Chemistry: Relevance to the Biomedical Sciences" Adv Polym Sci, vol. 186, pp. 151-209, 2005.

* cited by examiner

*Primary Examiner* — Leigh Maier
(74) *Attorney, Agent, or Firm* — Hueschen and Sage

(57) ABSTRACT

The present invention is directed to the use of chitosan, a chitosan derivative or a physiologically acceptable salt thereof, to increase nail growth rate. The invention is further directed to the use of chitosans to accelerate nail growth rate during treatment of nail illnesses, nail dystrophy or other nail conditions, in order to shorten considerably the specific treatments of said nail illnesses, nail dystrophy or other nail conditions.

10 Claims, 1 Drawing Sheet

USE OF CHITOSANS TO INCREASE NAIL GROWTH RATE

Figure 1:
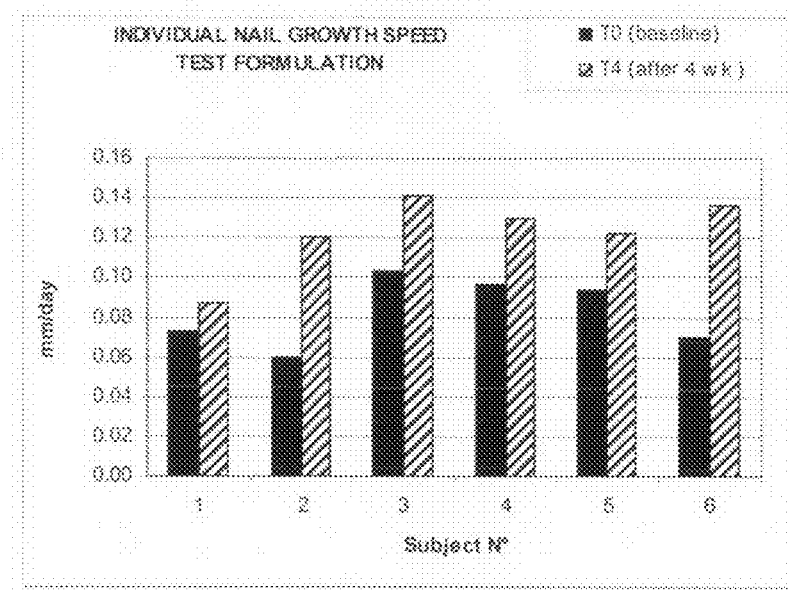

The present invention relates to the use of chitosan, a chitosan derivative and/or a physiologically acceptable salt thereof, to increase nail growth rate and to the use thereof for the treatment of growth disturbances of the nails. The invention further relates to the use of chitosans to shorten considerably the specific treatments of nail illnesses, nail dystrophy or other nail conditions.

BACKGROUND OF THE INVENTION

Nails are skin appendages made by horny, hard tissue, a material derived from dead corneocytes and composed by keratin, a protein rich of sulphated aminoacids and S—S bonds. Nails grow in a pocket-life invagination of the epidermis, just under the cuticle on the dorsal surface of the distal ends of fingers and toes. The formation of the nail material for the nail plate is performed primarily as an extrusion from a nail matrix, a specialized tissue which occupies the lower portion of the nail pocket from its proximal end up the lunula. The most proximal component of the matrix provides the corneocytes of the dorsal nail surface. These usually provide a shiny surface. When the matrix is altered by disease or the nail surface is subject to trauma, this shine is lost. The nail matrix region is near to the nail bed, with which the nail plate strongly adheres up to the hyponychium. This last is the dorsal region of the epidermis lying between the nail bed and finger pad.

The growth rate of the nail plate, such as the increase in length beyond its free edge, depends on the extent of regeneration of nail cells in the nail matrix. The cell material formed there differentiates into plate-like horny structures which are passively pushed in the distal direction. The nail grows continually during the entire life of the organism, the growth rate decreasing with old age, and in certain conditions like impaired peripheral circulation, nail infection, psoriasis and other illnesses. Changes in the fingernails of old people are mostly related to diminished tissue repair and inflammatory or degenerative changes of the distal interphalangeal joint. These influences are associated with reduced rate of longitudinal nail growth, thinning of the nail plate and accentuation of longitudinal ridges.

Variations in thickness and consistency of the toenails occur in elderly and are mostly attributable to changes in peripheral circulation.

Healthy looking nails should be smooth, curved, void of any spotting, and should not have any hollows or ridges. Nails in bad conditions can be very harmful for the personal image, if neglected can cause chronic infections, associated to long-lasting embarrassment and pain. Noteworthy, they may be considered a social problem and/or a professional illness. Since fingernails especially, but also toenails, are in constant contact with the environment, they are subjected to a great deal of minor and sometimes major trauma.

The average monthly increase in length of the fingernails is between 1-3 mm, and, in addition to age, circulation and specific illnesses, diet and physiological stresses can influence this value. The nails of the dominant hand are reported to grow faster. Toenails grow significantly more slowly than fingernails, thus while 6 months are needed by a thumb nail to complete re-growth, at least 12 months are needed by a big toenail, or by the other toenails, for their complete re-growth.

Nail growth plays a precise role in the treatment of onychomycosis and of other nail illnesses, as the complete re-growth of a healthy nail is part of the primary endpoint of each therapeutic protocol: thus, factors that can increase nail growth rate may have a decisive role in shortening the treatments of nail illnesses.

Chitosan derivatives, such as hydroxyalkyl chitosans and/or carboxyalkyl chitosans, are known in the art as water-soluble film forming agent. Their use is for instance disclosed in EP1303249, which discloses a nail varnish composition containing at least one antimycotic agent, and in WO2004/112814, which discloses a nail restructuring composition based on one herb extract from the genus *Equisetum* in combination with hydroxypropylchitosan, which is used as a film forming agent. The use of chitosans as film forming agents is also disclosed in WO2006111426 and in WO2007042682; the use of chitosans is also disclosed in Wenk, Myfungar Nagellak, Haut, Viavital Verlag, Essen, DE, Vol. 15, n. 7, 2004, pages 307-308; RU2108114; EP10679383; Monti et al., Drug Development and Industrial Pharmacy, 2005, United States, vol. 31, n. 1, 2005, pages 11-17; WO03051376.

It has now been found that the growth of nails may be accelerated by the application of products containing chitosan or chitosan derivatives, either alone or in combination with one or more active principles, on the nail plates.

DESCRIPTION OF THE INVENTION

The object of the present invention is represented by the use of chitosan, chitosan derivatives, and/or of a physiologically acceptable salt thereof, for the acceleration of nail growth.

The preferred chitosan derivatives are selected from chitosan amino-polysaccharides, preferably water soluble, having a molecular weight higher than 50000 Da, preferably of from 100000 to 500000 Da; among them hydroxyalkyl chitosans, such as hydroxypropyl chitosan, and carboxyalkyl chitosans are particularly preferred.

More particularly, it is represented by the use of chitosan, a chitosan derivative or of a physiologically acceptable salt thereof, for the acceleration of nail growth, during treatment not only of nail illnesses, such as onychomycosis, nail psoriasis, lichen planus, or atopic dermatitis, but also of nail dystrophy and nail growth disturbances of various origin.

Liquid or semi-solid preparations of chitosan or of a chitosan derivative, in the form of nail lacquer, cream, ointment, gel, lotion, foam, with a content in chitosan from 0.1 to 10 wt. %, more preferably from 0.2 to 5 wt. %, most preferably from 0.3 to 2%, are suitable to accelerate nail growth when regularly applied on the nail surface.

Pharmaceutical compositions will be prepared according to conventional techniques, using compatible excipients and pharmaceutically acceptable carriers, and may contain, in combination, one or more active principles with complementary or, in any case, useful activity.

The active agents which may be used in the compositions in combinations with the chitosans of the present invention include, but are not limited to, corticosteroids, antipsoriatic agents, immunosuppressive agents, antimycotic agents, antiseptic agents, moisturizers, and/or nail strengthening agents.

Examples of corticosteroids include 21-acetoxypregnenolone, alclometasone or its dipropionate salt, algestone, amcinonide, beclomethasone or its dipropionate salt, betamethasone and salts thereof, including, for example, betamethasone benzoate, betamethasone dipropionate, betamethasone sodium phosphate, betamethasone sodium phosphate and acetate, and betamethasone valerate; clobetasol or its propionate salt, clocortolone pivalate, hydrocortisone and salts thereof, including, for example, hydrocortisone acetate, hydrocortisone butyrate, hydrocortisone cypionate, hydrocortisone phosphate, hydrocortisone sodium phosphate, hydrocortisone sodium succinate, hydrocortisone tebutate and hydrocortisone valerate; cortisone acetate, desonide, desoximetasone, dexamethasone and salts thereof, for example, acetate and sodium phosphate; diflorasone diacetate, fludrocortisone acetate, flunisolide, fluocinolone acetonide, fluocinonide, fluorometholone, flurandrenolide, halcinonide, medrysone, methylprednisolone and salts thereof, e.g. acetate, sodium succinate; mometasone furoate, paramethasone acetate, prednisolone and salts thereof, e.g., acetate, diethylaminoacetate, sodium phosphate, sodium succinate, tebutate, trimethylacetate; prednisone, triamcinolone and derivatives thereof, e.g. acetonide, benetonide, diacetate, hexacetonide.

Examples of antipsoriatic agents include: anthracene derivatives, such as dithranol; psoralens, like trioxsalen or methoxsalen; Vitamin D3 analogues, like calcitriol, calcipotriol or tacalcitol; retinoids, like tazarotene, acitretine or etretinate; fumaric acid and esters thereof, e.g. monomethyl ester, dimethyl ester.

Examples of immunosuppressive agents include ciclosporin, tacrolimus, pimecrolimus and sirolimus.

Examples of antimycotic agents include: 1-hydroxy-2-pyridone compounds and their salts, e.g. ciclopirox, rilopirox, piroctone, ciclopirox olamine; imidazole derivatives and their salts, e.g. clotrimazole, econazole, isoconazole, ketoconazole, miconazole, tioconazole, bifonazole, fenticonazole and oxiconazole; polyene derivatives and their salts, e.g. nystatin, natamycin and amphotericin; allylamine derivatives and their salts, e.g. naphtifine and terbinafine; triazole derivatives and their salts, e.g. fluconazole, itraconazole, terconazole and voriconazole; morpholine derivatives and their salts, e.g. amorolfine and morpholines disclosed in U.S. Pat. No. 5,120,530; griseofulvin and related compounds, e.g. griseofulvin; undecylenic acid and its salts, in particular, the zinc and calcium salts of undecylenic acid; tolnaphtate and its salts; and flucytosine and its salts.

The antimycotic agent may also be selected from natural sources, in particular plant extracts. Examples of these extracts include tea tree oil (*Melaleuca attemifolia*), lavender oil (*Lavandula officinalis chaix*) and the leaf extract of the neem tree (*Azadirachta indica*).

Examples of the antiseptic agents include: benzalkonium-chlorid, benzethonium-chlorid, cetrimoniumbromid, chlorhexidin, dequaliniumchlorid, triclocarban, triclosan, salicylic acid, benzoic acid and their salts, p-hydroxybenzoic acid and its esters.

Examples of the compositions prepared according to the present invention include: nail lacquer, cream, ointment, gel, lotion, foam, for application to the nail surface freely or under semi-occlusive or occlusive medication.

The pharmaceutical compositions and the uses of the present invention will now be more fully described by the following examples. It should, however, be noted that such examples are given by way of illustration and not of limitation.

EXAMPLE 1

A solution having the following composition wt./wt. % is prepared:

| 1. purified water | 21.0% |
|---|---|
| 2. ethanol | 73.0% |
| 3. ethyl acetate | 4.0% |

-continued

| 4. hydroxypropyl chitosan (HPCH) | 1.0% |
|---|---|
| 5. cetostearyl alcohol | 1.0% |

Preparation

The formulation is prepared by using a closed vessel with a stirrer. To this vessel are added ethanol, deionized water and ethyl acetate to form a mixture. Thereafter, cetostearyl alcohol is added. Finally, hydroxypropyl chitosan is added and the resulting mixture is stirred for 24 hours or until dissolution.

The obtained composition has a clear and homogenous appearance even after prolonged storage. Moreover, when applied on the nails, the liquid is able to form a non-sticky and elastic film which could strongly adhere to the nail surface.

EXAMPLE 2

An open, comparative clinical study was performed to assess the nail growth accelerating efficacy and the safety of the solution according to the Example 1 on the nails of healthy volunteers. The trial was conducted by a single centre, under dermatological control for 4 weeks of treatment.

In particular the study product was applied, once daily, on 5 nails of the left or right hand according to a randomisation list and following the Investigator's instructions; the study product application side was assigned by the Investigator at each included subject during the baseline visit. Nails of the opposite hand were used as control area (untreated nails).

During the trial the following visits were performed:
baseline—T0a (before product use)
baseline extension visit—T0b (3 days after T0a)
final visit—T4a (after 25 days of treatment)
final extension visit—T4b (at the end of 4 week treatment).

The study was conducted on 22 healthy volunteers (1 male and 21 female), whose informed consent had been obtained, age range 18-50 (mean=43). All subjects ended the trial as per the protocol direction. No important event which may have interfered to the test results occurred during the study period.

The data processing was performed by descriptive and inferential analysis.

The activity of the product was expressed in absolute values and in relative terms with respect to an untreated control area. In particular statistical analysis of experimental data was performed as follows:

Comparison of T4 results of treated and untreated nails versus basal conditions (Student t test).

Comparison of treated vs untreated nails time by time (Variance analysis).

Nail growth speed (mm/day) was determined for each subject comparing the digital images of the thumb nail of both treated and untreated hands, taken in baseline conditions (T0a vs T0b) and at the end of the trial (T4a vs T4b).

The obtained results showed that the study product determined a statistically significant increase (Student t test $p<0.01$ vs T0) of nail growth speed corresponding to 15% (from a basal mean value of 0.071 mm/day to a final mean value of 0.082).

No variation of nail growth speed was highlighted for the untreated nails; in fact the mean value obtained at T0 and at T4 was 0.075 mm/day. Besides the increase of nail growth speed, an important increase of nail smoothness was measured in the treated nails, significant vs control, untreated nails. Moreover, the treatment was very well tolerated and no side effect was reported.

EXAMPLE 3

A solution having the following composition wt./wt. % is prepared:

| | |
|---|---|
| 1. purified water | 13.0% |
| 2. ethanol | 73.0% |
| 3. ciclopirox | 8.0% |
| 4. ethyl acetate | 4.0% |
| 5. hydroxypropyl chitosan (HPCH) | 1.0% |
| 6. cetostearyl alcohol | 1.0% |

Preparation

The formulation is prepared by using a closed vessel with a stirrer. To this vessel are added ethanol, deionized water and ethyl acetate to form a mixture. Thereafter, cetostearyl alcohol and ciclopirox are added. Finally, hydroxypropyl chitosan is added and the resulting mixture is stirred for 24 hours or until dissolution.

The obtained composition has a clear and homogenous appearance even after prolonged storage. Moreover, when applied on the nails, the liquid is able to form a non-sticky and elastic film which could strongly adhere to the nail surface.

EXAMPLE 4

The nail growth accelerating efficacy of the solutions according to the Examples 3 (named P-3051) and 1 (used as a placebo) was measured in the frame of a controlled clinical study on patients with onychomycosis due to dermatophyte fungi.

The study was multicentre, randomized, long-term, double blind/blinded assessment, parallel groups, three arms: the P-3051 solution as in the Example 3, containing hydroxypropylchitosan as an ingredient and ciclopirox as active antifungal agent; the placebo solution as in Example 1, containing hydroxypropylchitosan as an ingredient, but devoid of any active antifungal agent, and a reference nail lacquer from the US market (Penlac®), containing ciclopirox 8% as antifungal agent, and water, isopropanol, monoester resin as other ingredients. The reference solution differed from the test P-3051 solution in that no chitosan was contained in the reference. Overall, 467 patients were randomized in a 2:2:1 ratio among P-3051, reference product and placebo. They underwent a 4-8 week run in, 48 week treatment and 12 week follow up. Among efficacy endpoints, conversion to negative of fungal culture, percentage of patients with ≥0.90% clear nail, growth rate of healthy nail were measured during treatment and follow up. Growth rate of healthy nail is a parameter in which contribution of both the antimycotic effect and the nail growth accelerating effect plays a specific role.

As expected, the effect of P-3051 and reference active treatments on mycological findings was similar, with about 90% conversion to negative of fungal culture at end of treatment. The rate of conversion to negative of mycological culture was significantly lower (70%) in placebo arm, and this result was also expected.

The results in terms of nail growth rate are summarized in the table 1.

TABLE 1

Growth rate of healthy nail during treatment with P-3051, a nail lacquer containing ciclopirox 8% and hydroxypropylchitosan 1%; placebo, a nail lacquer containing hydroxypropylchitosan 1%; reference Penlac, a nail lacquer containing ciclopirox 8%.

| Growth of healthy nail | Placebo (n = 94) | P-3051 (n = 175) | Penlac (n = 185) |
|---|---|---|---|
| Week 24 | | | |
| Mean ± SD (N) | 4.89 ± 16.21 (88) | 6.29 ± 17.19 (167) | 4.73 ± 16.91 (177) |
| Week 36 | | | |
| Mean ± SD (N) | 6.56 ± 18.25 (77) | 9.17 ± 18.01 (162) | 5.93 ± 19.51 (170) |
| Week 48 | | | |
| Mean ± SD (N) | 7.3 ± 20.83 (74) | 11.6 ± 21.84 (157) | 8.28 ± 19.4 (156) |

The market reference, containing 8% ciclopirox, but not chitosan, had a continuous increase of growth of healthy nail, at 24, 36 and 48 week of treatment. Placebo, containing hydroxypropylchitosan, but not the active antifungal agent, showed also a continuous increase of growth of healthy nail, similar to that of the market reference. As it shall be appreciated, P-3051, containing both the chitosan and 8% ciclopirox (the active antifungal agent), was definitely more active than market reference Penlac®, in healthy nail growth rate.

It is concluded that the presence of chitosan derivative, having a direct effect on the nail growth rate, in the composition of P-3051, made according to the Example 3, improved the effect of the antimycotic agent in terms of growth of healthy nail.

EXAMPLE 5

A formulation having the following composition wt./wt. % is prepared:

| | |
|---|---|
| 1. purified water | 29.375% |
| 2. ethanol 96° | 70.0% |
| 3. budesonide | 0.025% |
| 4. hydroxypropyl chitosan (HPCH) | 0.5% |
| 5. Peg-40 Hydrogenated castor oil | 0.1% |

Preparation

The formulation is prepared as per the Examples 1 and 3, by adding hydroxypropyl chitosan as the final ingredient and stirring for 24 hours or until dissolution.

EXAMPLE 6

A formulation having the following composition wt./wt. % is prepared:

| 1. propylene glycol | 13.0% |
|---|---|
| 2. isopropanol | 82.497% |
| 3. calcitriol | 0.003% |
| 4. ethyl acetate | 4.0% |
| 5. chitosan | 0.5% |

Preparation

Chitosan is dissolved in propylene glycol, then calcitriol previously dissolved in isopropanol is added. Then ethyl acetate is added and the resulting mixture is stirred until dissolution.

EXAMPLE 7

An open, comparative clinical study was performed to assess the nail growth accelerating efficacy of the solution according to the Example 3 on the nails of 24 healthy male volunteers, aged 21-40 years (mean 31.8±SD 4.6 yrs) who gave their informed consent. In this experiment, the nail growth accelerating efficacy of the solution according to the Example 3 was compared with that of a commercial nail lacquer (Loceryl-France) as a reference, containing the following ingredients: amorolfine HCl 5.574%, metachrilic acid copolymer, triacetine, butyl acetate, ethyl acetate, ethanol. Test and reference products were randomly self-applied to all fingernails of either hand for a period of 28 days. The test product was applied once daily by a brush; the commercial reference was applied twice weekly as per the approved labelling, by using a spatula. Both test and reference products were applied in the evening. Before each test application the subjects were instructed to wash their hands with water and soap and dry accurately; before each reference application the subjects had to remove the previous product layer with an isopropyl alcohol swab.

The accelerating nail growth activity was assessed at the same timing and with the same method as per the Example 2.

The obtained results showed that the test solution according to the Example 3 determined a statistically significant increase (Student t test $p<0.01$ vs T0) of nail growth speed corresponding to 34% (from a basal mean value of 0.094 mm/day to a final mean value of 0.126).

On the contrary, the growth of the nails applied the reference nail lacquer did not significantly differ from baseline (0.104 mm/day) to the end of the experiment (0.117 mm/day, not significant).

EXAMPLE 8

A formulation having the following composition wt./wt. % is prepared:

| 1. propylene glycol | 13.0% |
|---|---|
| 2. isopropanol | 82.5% |
| 3. ethyl acetate | 4.0% |
| 4. chitosan | 0.5% |

Preparation

Chitosan is dissolved in propylene glycol, then isopropanol and ethyl acetate are added and the resulting mixture is stirred until dissolution.

EXAMPLE 9

An open, comparative clinical study was performed to assess the nail growth accelerating efficacy of the solution according to the Example 8 on the nails of 6 healthy male volunteers, aged 22-40 years (mean 32.2±SD 7.9 yrs) who gave their informed consent. In this experiment, the nail growth accelerating efficacy of the solution according to the Example 8 was randomly self-applied in the evening, before going to bed, to all fingernails of one hand for a period of 28 days. Before each test application the subjects were instructed to wash their hands with water and soap and dry accurately.

The accelerating nail growth activity was assessed at the same timing and with the same method as per the Example 2. Untreated fingernails served as reference nails.

The obtained results are summarized in FIG. 1. The test solution according to the Example 8 determined a statistically significant increase (Student t test $p<0.01$ vs T0) of nail growth speed by about 48% (from a basal mean value of 0.083 mm/day to a final mean value of 0.123).

On the contrary the growth of the reference untreated nails did not significantly differ from baseline (0.087 mm/day) to the end of the experiment (0.081 mm/day).

EXAMPLE 10

A liquid formulation having the following w/w % composition was prepared:

| 1) *Equisetum arvense* (Horsetail) glycolic extract | 5.00% |
|---|---|
| 2) Methylsulfonyl methane (MSM) | 5.00% |
| 3) Ethyl Alcohol 96° | 36.50% |
| 4) Diethyleneglycole monoethyletere[1] | 0.50% |
| 5) Chitosan | 1.00% |
| 6) Purified water | 52.00% |

[1]Transcutol ® P

Preparation

Chitosan was dissolved in water after acidification with acetic acid at pH 3.0. Then, ethyl alcohol was added and the mix was stirred till to obtain a clear viscous solution. At this point, the pH rose till to 5.5.

Diethyleneglycole monoethyletere, MSM and the glycolic extract were added and mixed till to obtain a clear slightly viscous solution.

The obtained formulation was a clear and yellow-pale solution, homogenous in appearance and slightly viscous.

EXAMPLE 11

An open, comparative clinical study was performed to assess the nail growth accelerating efficacy of the solution according to the Example 10 on the nails of 5 healthy female volunteers, aged 28-50 years, who gave their informed consent. In this experiment, the nail solution according to the Example 10 was randomly self-applied in the evening, before going to bed, to all fingernails of one hand for a period of 28 days. During the whole study the subjects were requested not to apply nail polishes nor to undergo treatments that could interfere with the assessment of the results.

The accelerating nail growth activity was assessed at the same timing and with the same method as per the Example 2. Untreated fingernails served as reference nails.

Figure 2:
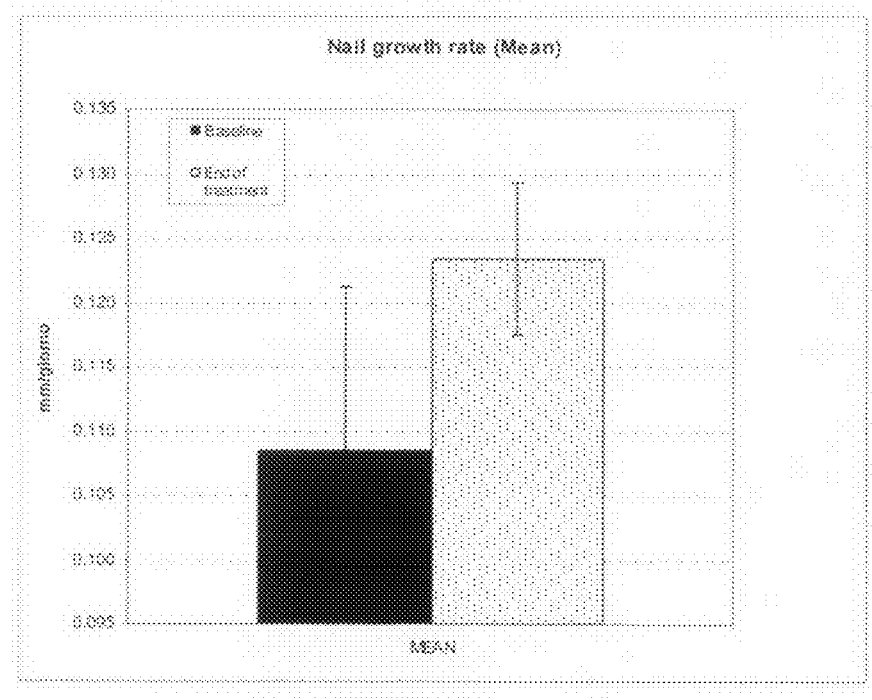

The obtained results are summarized in FIG. 2. The test solution according to the Example 10 determined a statistically significant increase (Student t test p<0.05 vs T0) of nail growth speed by 13.73% (from a basal mean value of 0.1085 mm/day to a final mean value of 0.1234).

On the contrary the growth of the reference untreated nails did not significantly differ from baseline (0.1097 mm/day) to the end of the experiment (0.1106 mm/day).

The invention claimed is:

1. A method for accelerating the nail growth rate consisting of applying to a nail a composition consisting of chitosan, a water soluble chitosan derivative which exhibits a molecular weight greater than 50.000 Daltons (Da), and/or a physiologically acceptable salt thereof, compatible excipients and pharmaceutically acceptable carriers, in an amount effective to accelerate the nail growth rate.

2. The method of claim 1, wherein the water soluble chitosan derivative exhibits a molecular weight from 100,000 to 500,000 Da.

3. The method of claim 2, wherein the water soluble chitosan derivative which exhibits a molecular weight greater than 50,000 Daltons (Da) is a hydroxyaikyl chitosan.

4. The method of claim 3, wherein the hydroxyalkyl chitosan is a hydroxypropyl chitosan.

5. The method of claim 2, wherein the water soluble chitosan derivative which exhibits a molecular weight greater than 50,000 Daltons (Da) is a carboxyalkyl chitosan.

6. The method of claim 1, wherein the composition consisting of chitosan, a water soluble chitosan derivative which exhibits a molecular weight greater than 50,000 Daltons (Da), and/or physiologically acceptable salt thereof, compatible excipients and pharmaceutically acceptable carriers is in the form of a topical formulation.

7. The method of claim 6, wherein the topical formulation is a nail lacquer, a spray, a cream, an ointment, a gel, a lotion or a foam.

8. The method of claim 6, wherein the topical formulation consists of chitosan, a water soluble chitosan derivative which exhibits a molecular weight greater than 50,000 Daltons (Da), and/or a physiologically acceptable salt thereof, in an amount from 0.1 to 10 wt. % with respect to the total weight of the topical formulation, compatible excipients and pharmaceutically acceptable carriers.

9. The method of claim 6, wherein the topical formulation consists of chitosan, a water soluble chitosan derivative which exhibits a molecular weight greater than 50,000 Daltons (Da), and/or a physiologically acceptable salt thereof, in an amount from 0.2 to 5 wt. % with respect to the total weight of the topical formulation, compatible excipients and pharmaceutically acceptable carriers.

10. The method of claim 6, wherein the topical formulation consists of chitosan, a water soluble chitosan derivative which exhibits a molecular weight greater than 50,000 Daltons (Da), and/or a physiologically acceptable salt thereof, in an amount from 0.3 to 2 wt. % with respect to the total weight of the topical formulation, compatible excipients and pharmaceutically acceptable carriers.

* * * * *